United States Patent

Pastor et al.

Patent Number: 5,292,785
Date of Patent: Mar. 8, 1994

[54] BIS-PHOSPHITE STABILIZED COMPOSITIONS

[75] Inventors: Stephen D. Pastor, Danbury, Conn.; Sai P. Shum, Hawthorne, N.Y.

[73] Assignee: Ciba-Geigy Corporation, Ardsley, N.Y.

[21] Appl. No.: 983,108

[22] Filed: Nov. 30, 1992

Related U.S. Application Data

[63] Continuation of Ser. No. 878,675, May 5, 1992, abandoned.

[51] Int. Cl.$^5$ .................... C08K 5/5393; C08K 5/527
[52] U.S. Cl. ................................................. 524/117
[58] Field of Search .................. 524/117, 126, 128

[56] References Cited

U.S. PATENT DOCUMENTS

| | | | |
|---|---|---|---|
| 3,297,631 | 1/1967 | Bown et al. | 524/131 |
| 3,476,699 | 11/1969 | Kauder et al. | |
| 3,907,939 | 9/1975 | Robin et al. | 558/85 |
| 4,143,028 | 3/1979 | Spivack. | |
| 4,196,117 | 4/1980 | Spivack. | |
| 4,318,845 | 3/1982 | Spivack et al. | |
| 4,351,759 | 9/1982 | Spivack | 524/117 |
| 4,374,219 | 2/1983 | Spivack et al. | |
| 4,381,359 | 4/1983 | Idel et al. | 558/85 |
| 4,524,166 | 6/1985 | Spivack et al. | |
| 4,599,206 | 7/1986 | Billig et al. | |
| 4,717,775 | 1/1988 | Billig et al. | |
| 4,748,261 | 5/1988 | Billig et al. | |
| 4,751,319 | 6/1988 | Odorisio et al. | |
| 4,769,498 | 9/1988 | Billig et al. | |
| 4,812,501 | 3/1989 | Odorisio et al. | |
| 4,835,299 | 5/1989 | Maker et al. | 558/85 |
| 4,912,155 | 3/1990 | Burton. | |
| 4,999,393 | 3/1991 | Haruna et al. | |
| 5,059,710 | 10/1991 | Abatoglow et al. | |
| 5,126,475 | 6/1992 | Bahrmann et al. | |

FOREIGN PATENT DOCUMENTS 9204403  3/1992  PCT Int'l Appl. .
0749844  7/1980  U.S.S.R. .

OTHER PUBLICATIONS

Odorisio et al., Phosphorous & Sulfur 1983 vol. 15, pp. 9-13.
Pastor, et al. Phosphorous & Sulfur 1983 vol. 15, pp. 253-256.
Odorisio et al. Phosphorous & Sulfur, 1984, vol. 91, pp. 285-293.
Phosphorous & Sulfur, 1984 vol. 19, pp. 1-10 Odorisio et al.
Spivack et al. Polymer Stabilization & Degradation pp. 249-254.
Pastor, et al. J. Heterocyclic Chem., 20 1311-1313, 1983.

*Primary Examiner*—Veronica P. Hoke
*Attorney, Agent, or Firm*—Luther A. R. Hall

[57] ABSTRACT

A stabilized composition of matter which comprises an organic material subject to oxidative, thermal or actinic degradation, and an effective stabilizing amount of a bisphosphite typified by formula I

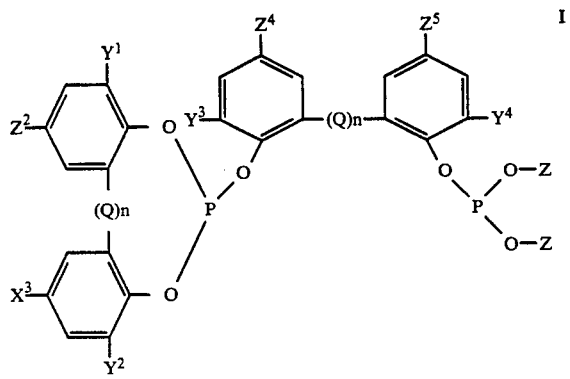

wherein n has a value of 0 or 1; Q is $-CR^1R^2$ where $R^1$ and $R^2$ are independently hydrogen, alkyl or aryl; $Y^1$, $Y^2$, $Y^3$, $Y^4$, $Z^2$, $Z^3$, $Z^4$ and $Z^5$ are independently hydrogen, alkyl, cycloalkyl, aralkyl, aryl, cyano, acyl and hydrogen; and each Z represents an identical or different alkyl, aryl, aralkyl or alkaryl group.

12 Claims, No Drawings

BIS-PHOSPHITE STABILIZED COMPOSITIONS

This is a continuation of application Ser. No. 07/878,675, filed on May 5, 1992, now abandoned.

The instant invention pertains to stabilized compositions of matter which comprise an organic material subject to oxidative, thermal or actinic degradation, and an effective stabilizing amount of a bisphosphite.

BACKGROUND OF THE INVENTION

The use of organic trivalent phosphorus compounds, e.g. organic phosphites and phosphonites, for the stabilization of degradable polymeric substrates is well known. U.S. Pat. Nos. 4,143,028; 4,196,117; 4,318,845; 4,374,219; 4,524,166; 4,912,155; and 4,999,393 and references cited therein describe the use of seven- and eight-membered dibenzo[df][1,3,2]dioxaphosphepins and dibenzo[d,g][1,3,2]dioxaphosphocins for the stabilization of degradable polymers.

Spivack et al. in *Polymer Stabilization and Degradation*, P. P. Klemchuk editor; American Chemical Society: Washington D.C., 1985, 247-257 has described the use of hydrolytically stable seven- and eight-membered dibenzo[d,f][1,3,2]dioxaphosphepins and dibenzo[d,g][1,3,2]dioxaphosphocins, respectively, as processing stabilizers.

The detailed synthesis of seven- and eight-membered dibenzo[d,f][1,3,2]dioxaphosphepins and dibenzo[d,g][1,3,2]dioxaphosphocins is described by Pastor et al. in *Phosphorus Sulfur*, 1983, 15, 9; *Phosphorus Sulfur*, 1983, 15, 253; *J. Heterocycl.* 1983, 20, 1311; *Phosphorus Sulfur*, 1984, 19, 1; and *Phosphorus Sulfur*, 1984, 19, 285.

U.S. Pat. Nos. 4,751,319 and 4,812,501 describe stabilized compositions containing biaryl derivatives of 1,3,2-oxazaphospholidines, which are structurally distinct from the compounds of this invention. U.S. Pat. Nos. 4,599,206; 4,717,775; 4,748,261; 4,769,498 and 5,059,710 describe ligands of formula I, and III useful for transition-metal-catalyzed hydroformylation reactions. The use of compounds of formula I, and III for the stabilization of degradable organic materials is neither described nor suggested.

The instant stabilized compositions essentially comprise a degradable polymeric substrate and a compound of formula I, and III described in this invention provide superior stabilization. This is manifested in the superior processing stability of these polymeric compositions in terms of melt flow stabilization and resistance to discoloration. In addition the compositions of the instant invention exhibit superior resistance to hydrolysis prior to processing.

OBJECT OF THE INVENTION

The object of the invention is to provide stabilized compositions containing an degradable organic polymeric material, and an effective stabilizing amount of a bisphosphite of formula I, or III alone or in combination with a hindered phenolic antioxidant and/or a hindered amine thermal stabilizer.

DETAILED DISCLOSURE

The instant invention pertains to stabilized compositions of matter comprising
(A) an organic material subject to oxidative, thermal or actinic degradation, and
(B) an effective stabilizing amount of a bisphosphite of formula I, or III

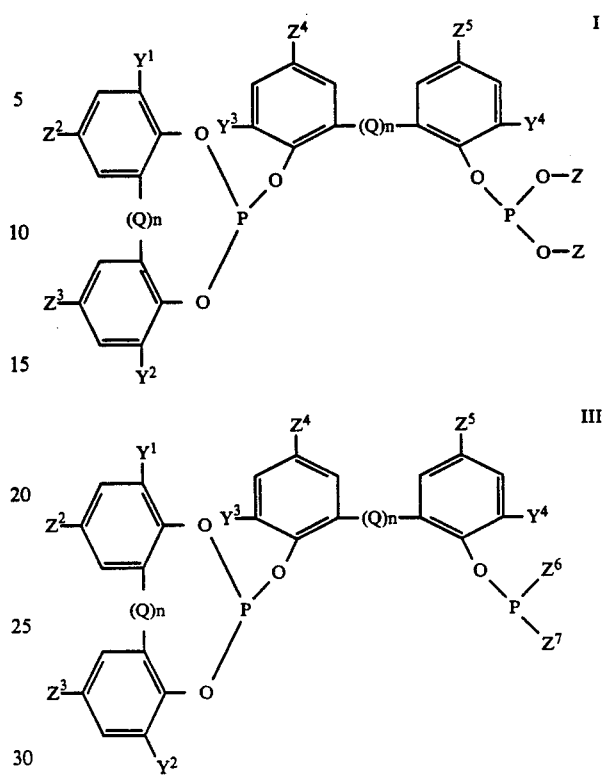

wherein
n has a value of 0 or 1;
when n is 0, Q is a direct bond,
when n is 1, Q is —$CR^1R^2$ wherein each $R^1$ and $R^2$ independently represents hydrogen, straight chain alkyl of 1 to 18 carbon atoms, branched chain alkyl of 1 to 12 carbon atoms, phenyl, tolyl or anisyl;
each $Y^1$, $Y^2$, $Y^3$, $Y^4$, $Z^2$, $Z^3$, $Z^4$ and $Z^5$ independently represents hydrogen, a straight or branched chain alkyl of 1 to 18 carbon atoms, bicycloalkyl of 7 to 10 carbon atoms, phenyl, benzyl, 1-phenylethyl, cyclohexyl, 1-methylcyclohexyl, cyano, halogen, nitro, trifluoromethyl, hydroxy, amino, alkanoyl of 2 to 18 carbon atoms, alkoxy of 1 to 18 carbon atoms or $E^1E^2E^3Si$ where $E^1$, $E^2$ and $E^3$ are independently hydrogen, alkyl of 1 to 4 carbon atoms or phenyl;
each Z independently represents alkyl of 1 to 18 carbon atoms, phenyl or said phenyl mono- or di-substituted by alkyl of 1 to 8 carbon atoms or 1-phenylethyl; or by cyano, halogen, nitro, trifluoromethyl, hydroxy, amino, alkanoyl of 2 to 18 carbon atoms, alkoxy of 1 to 18 carbon atoms or $E^1E^2E^3Si$ where $E^1$, $E^2$ and $E^3$ are independently hydrogen, alkyl of 1 to 4 carbon atoms or phenyl; and
$Z^6$ and $Z^7$ are independently hydrogen, a straight or branched chain alkyl of 1 to 18 carbon atoms, phenyl, said phenyl substituted by alkyl of 1 to 8 carbon atoms; or are independently benzyl, 1-phenylethyl, cyclohexyl, 1-methylcyclohexyl, cyano, halogen, —$NR^3R^4$, and —$SR^5$ where $R^3$, $R^4$ and $R^5$ are independently hydrogen, a straight or branched chain alkyl of 1 to 18 carbon atoms, phenyl, benzyl, cyclohexyl or 1-methylcyclohexyl.

Preferably in the bisphosphites of formula I, and III, $Y^1$ and $Y^2$ are alkyl of 1 to 18 carbon atoms or 1- phenylethyl. A particularly preferred embodiment of the instant invention is when $Y^1$ and $Y^2$ are each tert-butyl.

Preferably Z is phenyl or said phenyl mono- or disubstituted by alkyl of 1 to 8 carbon atoms or 1-phenylethyl. A particularly preferred embodiment of the instant invention is where Z is phenyl.

Preferably $Z^2$, $Z^3$, $Z^4$ and $Z^5$ are independently straight or branched chain alkyl of 1 to 18 carbon atoms or 1-phenylethyl. A particularly preferred embodiment of the instant invention is where $Z^2$, $Z^3$, $Z^4$ and $Z^5$ are independently methyl or tert-butyl.

Preferably $Z^6$ and $Z^7$ are independently straight or branched chain alkyl of 1 to 18 carbon atoms, 1-phenylethyl, phenyl or phenyl substituted by alkyl of 1 to 8 carbon atoms; or are independently fluorine, $-NR^3R^4$ or $-SR^5$ wherein $R^3$, $R^4$, and $R^5$ are independently hydrogen, alkyl of 1 to 18 carbon atoms, phenyl, benzyl, cyclohexyl, or 1-methylcyclohexyl. A particularly preferred embodiment of the instant invention is where $Z^6$ and $Z^7$ are phenyl or N,N-diethylamino.

The integer n is zero or one;

When n is one, Q is preferably $-CR^1R^2$ wherein $R^1$ and $R^2$ independently represent hydrogen, straight chain alkyl of 1 to 18 carbon atoms, branched chain alkyl of 1 to 12 carbon atoms, or phenyl. Particularly preferred, $R^1$ is hydrogen, and $R^2$ is hydrogen, methyl or phenyl.

When any of $R^1$ to $R^5$, $Y^1$ to $Y^4$, and Z to $Z^7$ are alkyl, such alkyl groups are, for example, methyl, ethyl, isopropyl, n-butyl, isobutyl, tert-butyl, tert-amyl, 2-ethylhexyl, n-octyl, tert-octyl, lauryl, n-octadecyl, eicosyl and triacontyl; when said radicals are cycloalkyl, they are, for example, cyclopentyl, cyclohexyl, cyclooctyl and cyclododecyl; when said radicals are alkenyl, they are, for example, allyl, butenyl and oleyl; when said radicals are phenylalkyl, they are, for example, benzyl, phenethyl, α-methylbenzyl and α,α-dimethylbenzyl; when said radicals are aryl, they are, for example, phenyl, 2,4-di-tert-butylphenyl, and naphthyl; when said radicals are alkyl interrupted by —O— or —S—, they are, for example, 3-oxaamyl, 3,6-dioxaoctyl, 3-thiaamyl and 3,6-dithiaoctyl; when said radicals are bicycloalkyl or tricycloalkyl, they are, for example, isobornyl and adamantyl; when said radicals are halogen, they are, for example, fluorine, chlorine or bromo.

The preparation of compounds of general formulas I, and III is described in U.S. Pat. Nos. 4,599,206; 4,717,775; 4,748,261; 4,769,498 and 5,059,710.

The instant invention pertains to a stabilized composition which comprises (A) an organic material subject to oxidative, thermal or actinic degradation, and (B) an effective stabilizing amount of a compound of formula I, or III as described above.

The instant invention also relates to such a composition which additionally contains a phenolic antioxidant, a hindered amine stabilizer or a mixture thereof.

The organic material of component (A) is preferably a synthetic polymer; most preferably a polyolefin.

Substrates in which the compounds of this invention are particularly useful are polyolefins such as polypropylene and polyethylene; polystyrene, including especially impact polystyrene; ABS resin; elastomers such as e.g. butadiene rubber, EPM, EPDM, SBR and nitrile rubber.

The instant invention also pertains to stabilized compositions which additionally contain a phenolic antioxidant or a hindered amine compound or a combination thereof. Lists of appropriate phenolic antioxidants and of hindered amine compounds are given below.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyally-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methylindoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tertbutylbenzylphosphonic acid monoalkyl esters, such as of the methyl, ethyl or butyl ester, nickel complexes of ketoximes such as of 2-hydroxy-4-methylphenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl) sebacate.

2.7. Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the layryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flame-proofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tertbutyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-traizine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylene-bis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethylpiperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one) and bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis-(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl) sebacate.

The following examples are presented for the purpose of illustration only and are not to be construed to limit the nature or scope of the instant invention in any manner whatsoever.

EXAMPLE 1

3-Chloro-2,4,8,10-tetra-tert-butyl-dibenzo[d,f][1,3,2]dioxaphosphepin

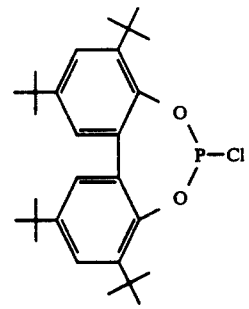

Into a solution of 20 g (49 mmol) of 2,2'-bis(4,6-di-tert-butylphenol) and 0.48 g (4.8 mmol) of 1-methyl-2-pyrrolidinone in 200 mL of toluene is added dropwise 10 g (73 mmol) of phosphorus trichloride at ambient temperature. After addition is complete, the reaction mixture is heated to 95° C. for 17 hours. A slow stream of nitrogen is used to removed hydrogen chloride. The reaction mixture is filtered and the filtrate is concentrated in vacuo to give 23.14 g (99% yield) of a white solid.

$^{31}$P NMR (200 MHz)(Benzene-d$_6$) (ppm): 173.3 ppm

EXAMPLE 2

1-O-(2,4,8,10-Tetra-tert-butyl-dibenzo[d,f][1,3,2]dioxaphosphepin-6-yl)-2,2'-ethylidenebis(4,6-di-tert-butylphenol)

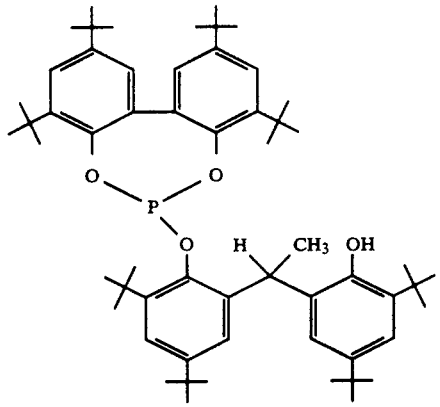

Into a solution of 27.6 g (63 mmol) of 2,2'-ethylidenebis(4,6-di-tert-butylphenol) and 8.8 mL (63 mmol) of triethylamine in 200 mL of toluene is added dropwise a solution of 30 g (63 mmol) of 3-chloro-2,4,8,10-tetra-tert-butyl-dibenzo[d,f][1,3,2]dioxaphosphepin in 100 mL of toluene at ambient temperature. After 20 hours of stirring at ambient temperature, the reaction mass is filtered to remove triethylamine hydrochloride and the filtrate is concentrated in vacuo to give 50 g of an oil. Trituration of the crude oil with 200 mL of acetonitrile gives 40.9 g (74% yield) of a white solid: m.p.=273°-277° C.

$^{31}$P NMR (200 MHz)(Benzene-d$_6$)(ppm): 144.3 ppm

Analysis: Calcd. for $C_{58}H_{85}O_4P$: C, 79.4; H, 9.8. Found: C, 79.1; H, 10.2.

EXAMPLE 3

2-O-(2,4,8,10-Tetra-tert-butyl-dibenzo[d,f][1,3,2]dioxa-phosphepin-6-yl)-3,3',5,5'-tetra-tert-butyl-2,2'-dihydroxy-1,1'-biphenyl

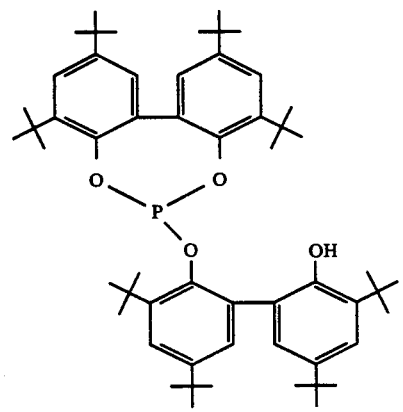

Into a solution of 120 g (252 mmol) of 3,3',5,5'-tetra-tert-butyl-2,2'-dihydroxy-1,1'-biphenyl and 81.6 mL (431 mmol) of triethylamine in 300 mL of toluene is added dropwise a solution of 19.2 mL (220 mmol) of phosphorus trichloride in 10 mL of toluene at ambient temperature. After 24 hours of stirring at ambient temperature, the reaction mixture is filtered to remove triethylamine hydrochloride and the filtrate is concentrated in vacuo to give a white mass. Trituration of the crude mass with 500 mL of acetonitrile gives 31.69 g (26% yield) of a white solid: m.p.=245°-250° C.

Analysis: Calcd. for $C_{56}H_{81}O_4P$: C, 79.2; H, 9.6. Found: C, 79.3; H, 10.0.

EXAMPLE 4

1-O-(2,4,8,10-Tetra-tert-butyl-dibenzo[d,f][1,3,2]dioxa-phosphepin-6-yl)-2,2'-methylenebis-(4,6-di-tert-butyl-phenol)

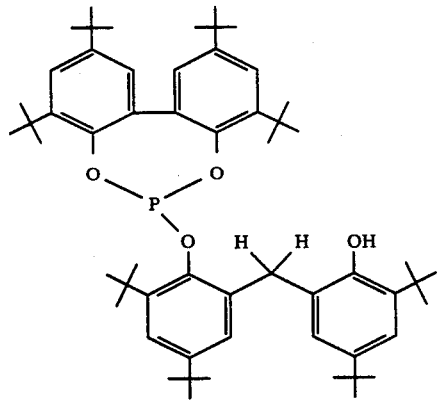

Into a solution of 21.23 g (50 mmol) of 2,2'-methylenebis(4,6-di-tert-butylphenol) and 7 mL (50 mmol) of triethylamine in 200 mL of toluene is added dropwise a solution of 23.84 g (50 mmol) of 3-chloro-2,4,8,10-tetra-tert-butyl-dibenzo[d,f][1,3,2]dioxaphos-phepin in 100 mL of toluene at ambient temperature. After 20 hours of stirring at ambient temperature, the reaction mass is filtered to remove triethylamine hydrochloride and the filtrate is concentrated in vacuo to give a brownish oil. Trituration of the crude oil with 200 mL of acetonitrile gives 36.65 g (85% yield) of a white solid: m.p.=195°-205° C.

Analysis: Calcd. for $C_{57}H_{83}O_4P$: C, 79.3; H, 9.7. Found: C, 78.8; H, 10.2.

EXAMPLE 5

1-O-(2,4,8,10-Tetra-tert-butyl-12-methyl-12H-diben-zo[d,g][1,3,2]dioxaphosphocin-6-yl)-2,2'-ethylidenebis(4,6-di-tert-butylphenol)

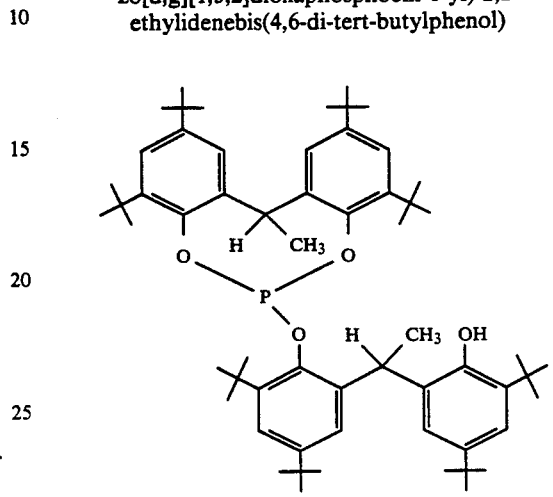

The procedure of Example 3 is repeated using 87.7 g (200 mmol) of 2,2'-ethylidene-bis(4,6-di-tert-butylphenol) and 41.8 mL (300 mmoL) of triethylamine in 300 mL of toluene and 8.7 mL (100 mmol) of phosphorus trichloride in 50 mL of toluene to give a yellowish oil. Trituration of the oil with 300 mL of acetonitrile gives 79.4 g (86% yield) of a white solid: m.p.=219°-221° C.

Analysis: Calcd. for $C_{60}H_{89}O_4P$: C, 79.6; H, 9.9. Found: C, 79.1; H, 10.2.

EXAMPLE 6

1-O-(2,4,8,10-Tetra-tert-butyl-12H-dibenzo[d,g][1,3,2-]dioxaphosphocin-6-yl)-2,2'-methylenebis(4,6-di-tert-butylphenol)

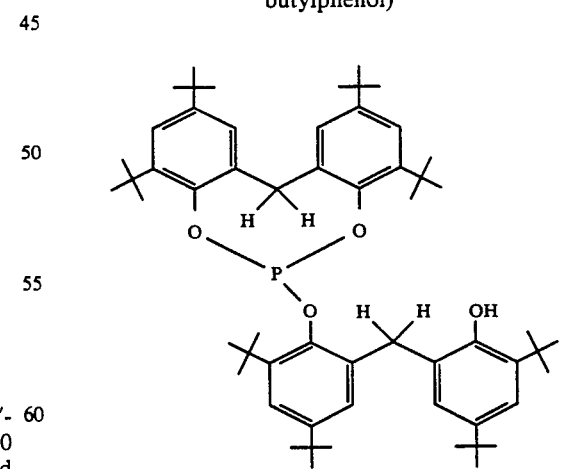

The procedure of Example 3 is repeated using 84.9 g (200 mmol) of 2,2'-methylenebis(4,6-di-tert-butyl-phenol) and 41.8 mL (300 mmol) of triethylamine in 200 mL of toluene and 8.7 mL (100 mmol) of phosphorus trichloride in 100 mL of toluene to give 90 g of an off-white solid. Trituration of the off-white solid with 200 mL of acetonitrile gives 80.4 g (92% yield) of a white solid: m.p.=243°-246° C.

Analysis: Calcd. for $C_{58}H_{85}O_4P$: C, 79.4; H, 9.8. Found: C, 79.2; H, 10.0.

EXAMPLE 7

1-O-(2,4,8,10-tetra-tert-butyl-dibenzo[d,f][1,3,2]dioxaphosphepin-6-yl)-1'-O'-(dichlorophosphino)-2,2'-ethylidenebis(4,6-di-tert-butylphenol)

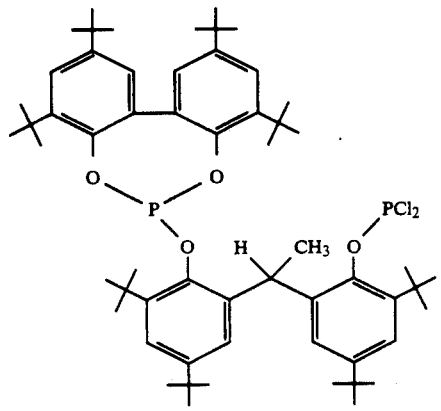

Into a solution of 30 g (34.2 mmol) of the compound of Example 2 and 12 mL (85.5 mmol) of phosphorus trichloride in 250 mL of xylene is added a solution of 7.5 mL (85.5 mmol) of phosphorus trichloride in 40 mL of xylene. After addition is complete, the reaction mixture is heated reflux for 96 hours. The reaction mixture is filtered and the filtrate is concentrated in vacuo to give an off-white solid. Trituration of the off-white solid with 200 ml acetonitrile gives 30 g (90% yield) of a white solid.

$^{31}P$ NMR (200 MHz)(Benzene-$d_6$)(ppm): 202.4 and 140.4 ppm; $^8J_{PP}$=136 Hz.

EXAMPLE 8

1-O-(2,4,8,10-Tetra-tert-butyl-dibenzo[d,f][1,3,2]dioxaphosphepin-6-yl)-1'-O'-(diphenoxyphosphino)-2,2'-ethylidenebis(4,6-di-tert-butylphenol)

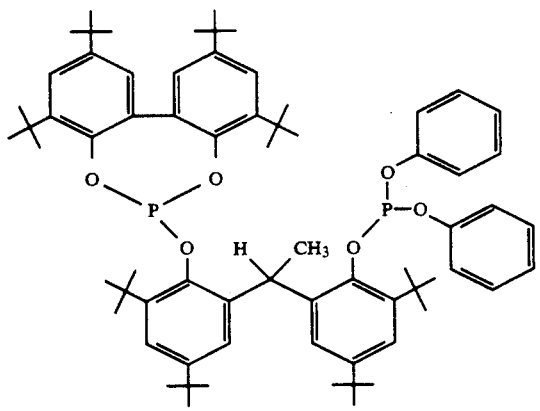

Into a solution of 28 g (28.6 mmol) of the compound of Example 7 in 300 mL of toluene is added dropwise a solution of 5.4 g (57.2 mmol) of phenol and 8 mL (57.2 mmol) of triethylamine in 20 mL of toluene at ambient temperature. After 18 hours of stirring at ambient temperature, the reaction mixture is filtered to remove triethylamine hydrochloride and filtrate is concentrated in vacuo to give 30 g of an off-white solid. Trituration of the crude product with 100 mL of acetonitrile gives 10.4 g (32% yield) of a white solid: m.p.=164°-167° C.

Analysis: Calcd. for $C_{70}H_{94}O_6P_2$: C, 76.9; H, 8.7. Found: C, 76.9; H, 9.0.

EXAMPLE 9

2-O-(2,4,8,10-Tetra-tert-butyl-dibenzo[d,f][1,3,2]dioxaphosphepin-6-yl)-2'-O'-(dichlorophosphino)-3,3',5,5'-tetra-tert-butyl-2,2'-dihydroxy-1,1'-biphenyl

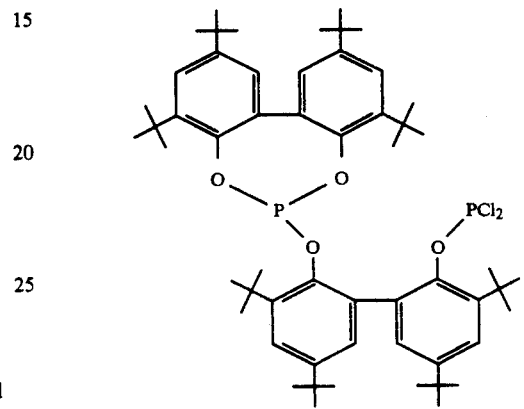

The procedure of Example 7 is followed using 26.7 g (31.5 mmol) of the compound of Example 3, and 8.8 mL (63 mmol) of triethylamine in 200 mL of toluene and 5.5 mL (63 mmol) of phosphorus trichloride in 20 mL of toluene. The crude residue is triturated with 200 mL of acetonitrile to give 25.3 g (85% yield) of an off-white solid: m.p.=220°-231° C.

$^{31}P$ NMR (200 MHz) (Benzene-$d_6$) (ppm): 203.85, 142.24 ppm; $^7J_{PP}$=4.8 Hz.

EXAMPLE 10

2-O-(2,4,8,10-Tetra-tert-butyl-dibenzo[d,f][1,3,2]dioxaphosphepin-6-yl)-2'-O'-(diphenoxy-phosphino)-3,3',5,5'-tetra-tert-butyl-2,2'-dihydroxy-1,1'-biphenyl

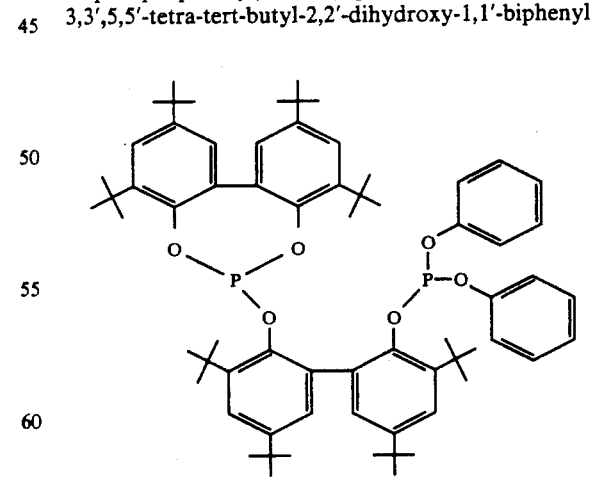

The procedure of Example 8 is repeated using 20 g (21 mmol) of the compound of Example 9 in 150 mL of toluene and 4 g (42 mmol) of phenol and 5.85 mL (42 mmol) of triethylamine in 200 mL of toluene to give 28 g of a yellowish solid. The crude product is purified by flash chromatography (silica gel, 0.5% ethyl acetate/99.5% hexane) to give 15.9 g (71% yield) of a white solid: m.p.=141°–145° C.

Analysis: Calcd. for $C_{68}H_{90}O_6P_2$: C, 76.7; H, 8.5. Found: C, 77.3; H, 9.0.

EXAMPLE 11

1-O-(2,4,8,10-tetra-tert-butyl-12-methyl-12H-dibenzo[d,g][1,3,2]dioxaphosphocin-6-yl)-1'-O'-(dichlorophosphino)-2,2'-ethylidenebis(4,6-di-tert-butylphenol)

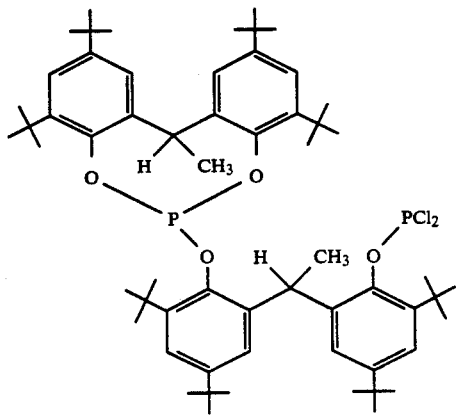

The procedure of Example 7 is repeated using 50 g (55 mmol) of the compound of Example 5 and 16 mL (114 mmol) of triethylamine in 200 mL of toluene and 9.9 mL (114 mmol) of phosphorus trichloride in 50 mL of toluene to give 62 g of an oil. Trituration of the crude oil with 200 mL of acetonitrile gives 48.6 g (87% yield) of a white solid: m.p.=195°–200° C.

$^{31}P$ NMR (200 MHz) (Benzene-$d_6$) (ppm): 203.86, 139.07 ppm; $^8J_{pp}$=18 Hz.

EXAMPLE 12

1-O-(2,4,8,10-Tetra-tert-butyl-12-methyl-12H-dibenzo[d,g][1,3,2]dioxaphosphocin-6-yl)-1'-O'-(diphenoxyphosphino)-2,2'-ethylidenebis(4,6-di-tert-butylphenol)

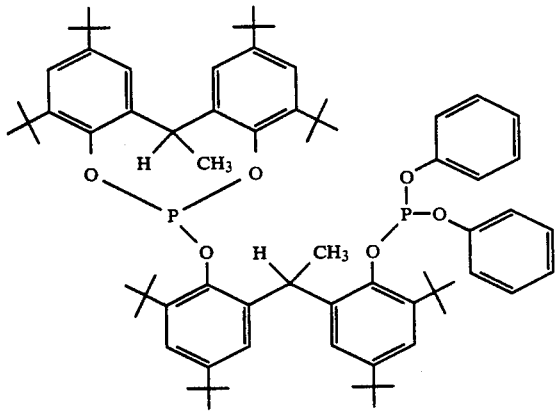

The procedure of Example 8 is repeated using 35 g (35 mmol) of the compound of Example 11 in 250 mL of toluene and 6.6 g (70 mmol) of phenol and 9.8 mL (70 mmol) of triethylamine in 50 mL of toluene to give a yellowish oil. Trituration of the crude oil with 200 mL of acetonitrile gives 33.8 g (86% yield) of a white solid: m.p.=152°–156° C.

Analysis: Calcd. for $C_{72}H_{98}O_6P_2$: C, 77.1; H, 8.8. Found: C, 77.5; H, 9.1.

EXAMPLE 13

1-O-(2,4,8,10-tetra-tert-butyl-dibenzo[d,f][1,3,2]dioxaphosphepin-6-yl)-1'-O'-(dichlorophosphino)-2,2'-methylenebis(4,6-di-tert-butylphenol)

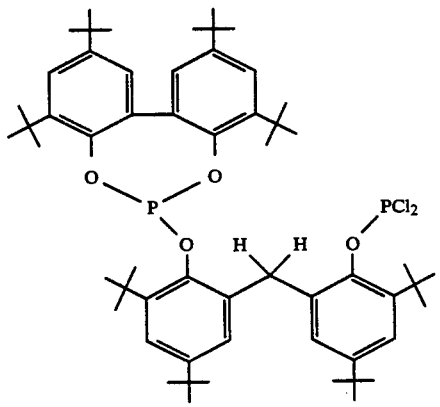

The procedure of Example 7 is repeated using 30 g (35 mmol) of the compound of Example 4 and 12.3 mL (88 mmol) of triethylamine in 200 mL of xylene and 7.7 mL (88 mmol) of phosphorus trichloride in 40 mL of xylene to give 38 g of a yellowish gum.

$^{31}P$ NMR (200 MHz) (Benzene-$d_6$) (ppm): 202.7, 142.8 ppm.

EXAMPLE 14

1-O-(2,4,8,10-Tetra-tert-butyl-dibenzo[d,f][1,3,2]dioxaphosphepin-6-yl)-1'-O'-(diphenoxyphosphino)-2,2'-methylenebis(4,6-di-tert-butylphenol)

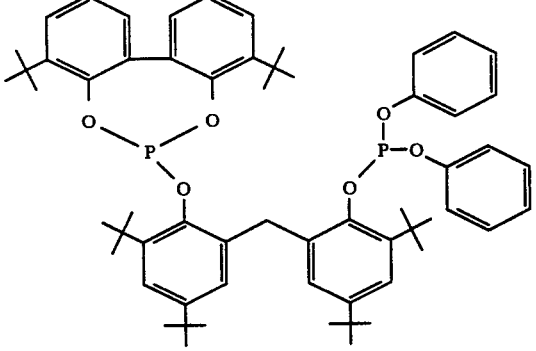

The procedure of Example 8 is repeated using 33.7 g (35 mmol) of the compound of Example 13 in 200 mL of toluene and 6.85 g (35 mmol) of phenol and 9.8 mL (70 mmol) of triethylamine in 20 mL of toluene to give 36.98 g of a off-white foam. The crude product is purified by flash chromatography (silica gel, 1% ethyl acetate/99% hexane) to give 3 g (15% yield) of a white crystalline foam: m.p.=70°–75° C.

Analysis: Calcd. for $C_{69}H_{92}O_6P_2$: C, 76.8; H, 8.6. Found: C, 76.5; H, 8.9.

EXAMPLE 15

1-O-(2,4,8,10-tetra-tert-butyl-12H-dibenzo[d,g][1,3,2]dioxaphosphocin-6-yl)-1',O'-(dichlorophosphino)-2,2'-methylenebis(4,6-di-tert-butylphenol)

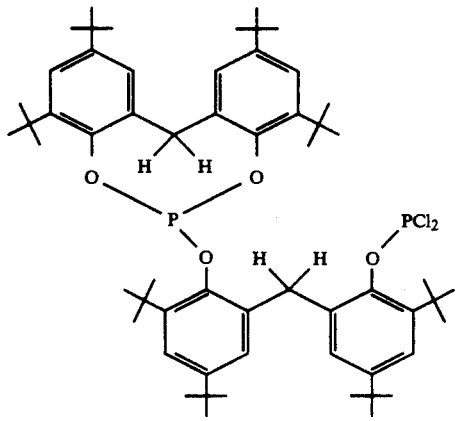

The procedure of Example 7 is repeated using 40 g (45.6 mmol) of the compound of Example 6, 7.9 mL (57 mmol) of triethylamine in 200 mL of toluene and 5 mL (57 mmol) of phosphorus trichloride in 10 mL of toluene to give 33.2 g (75% yield) an off-white solid.

$^{31}$P NMR (200 MHz) (Benzene-$d_6$) (ppm): 202.63, 137.30 ppm.

EXAMPLE 16

1-O-(2,4,8,10-Tetra-tert-butyl-12H-dibenzo[d,g][1,3,2-]dioxaphosphocin-6-yl)-1'-O'-(diphenoxyphosphino)-2,2'-methylenebis-(4,6-di-tert-butylphenol)

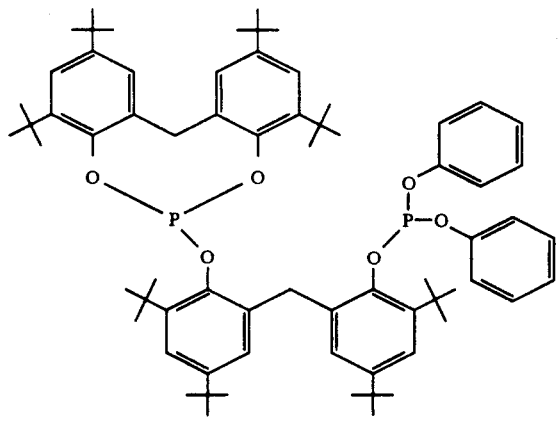

The procedure of Example 8 is repeated using 9.77 g (10 mmol) of the compound of Example 15 in 50 mL of toluene and 1.88 g (20 mmol) of phenol and 2.8 mL (20 mmol) of triethylamine in 50 mL of toluene to give 8.7 g of a solid. The product is identified by mass spectroscopy: m/z=1094.

EXAMPLE 17

1-O-(2,4,8,10-Tetra-tert-butyl-dibenzo[d,f][1,3,2]dioxaphosphepin-6-yl)-1'-O'-(diphenylphosphino)-2,2'-ethylidenebis(4,6-di-tert-butylphenol)

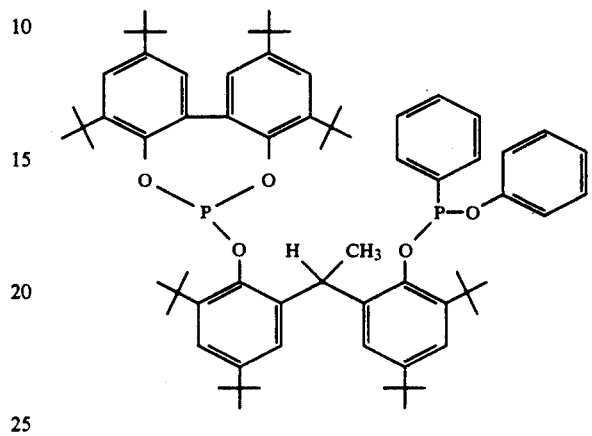

Into a solution of 3.6 g (4 mmol) of the compound of Example 7 in 25 mL of toluene is added dropwise a 1.8M solution of 4.4 mL (8 mmol) of phenyl lithium at ambient temperature. After the addition is complete, the reaction mixture is heated to reflux for 16 hours. The reaction mixture is filtered and the filtrate is concentrated in vacuo to give 5 g of a dark oil. The product is identified by mass spectroscopy: m/z=1061.

EXAMPLE 18

1-O-(2,4,8,10-Tetra-tert-butyl-12-methyl-12H-dibenzo[d,g][1,3,2]dioxaphosphocin-6-yl)-1'-O'-(diphenylphosphino)-2,2'-ethylidenebis(4,6-di-tert-butylphenol)

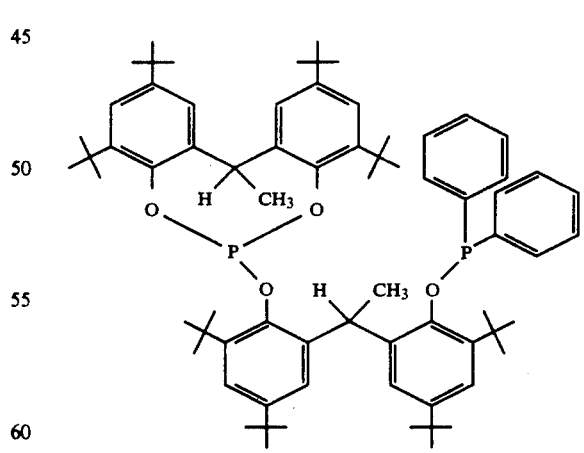

The procedure of Example 18 is repeated using 5 g (5 mmol) of the compound of Example 11 in 50 mL of toluene and 5.5 mL (10 mmol) of 1.8M solution of phenyl lithium to give 8 g of a dark oil. The product is identified by mass spectroscopy: m/z=1089.

EXAMPLE 19

1-O-(2,4,8,10-Tetra-tert-butyl-12-methyl-12H-dibenzo[d,g][1,3,2]dioxaphosphocin-6-yl)-1'-O'-(chloro-diethylaminophosphino)-2,2'-ethylidenebis(4,6-di-tert-butylphenol)

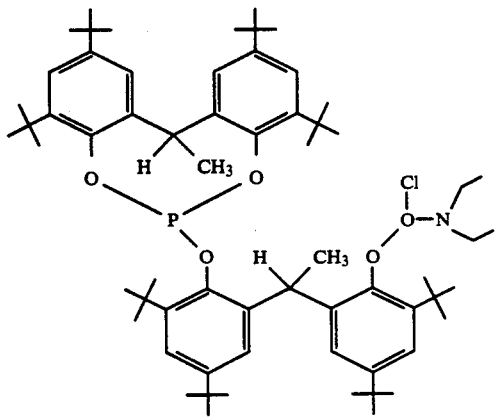

Into a solution of 2.53 g (2.8 mmol) of the compound of Example 11 in 50 mL of toluene is added a solution of 0.58 mL (5.6 mmol) of diethylamine and 0.78 mL (5.6 mmol) of triethylamine in 5 mL of toluene at ambient temperature. After the addition is complete, the reaction mixture is heated to 70° C. for 5 hours. The product is identified by mass spectroscopy: m/z=1042.

EXAMPLE 20

Process Stabilization of Polypropylene at 525° F. (274° C.)

The base formulation comprises unstabilized, new technology polypropylene (PROFAX® 6501, Himont) containing 0.075% by weight of calcium stearate. The test additives are incorporated into the polyproyplene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder (extruder screw to wall clearance adjusted tighter than normal for harsher than normal processing conditions) at 525° F. (274° C.) with a residence time of 90 seconds.

After each of the first and third extrusions, the melt flow rate (in grams/10 minutes) is determined by ASTM method D1238 on the pellets obtained from the extruder. The results are given in the table below.

| Additive | Concentration (% by weight) | Melt Flow after Extrusion 1 | 3 |
|---|---|---|---|
| None | — | 13.2 | 65.9 |
| Compound of Example 8 | 0.075 | 7.0 | 31.5 |
| Compound of Example 10 | 0.075 | 5.2 | 29.2 |
| Compound of Example 12 | 0.075 | 8.6 | 39.1 |
| Compound of Example 14 | 0.075 | 6.1 | 32.9 |

These results show that the stabilized compositions of the instant invention provide improved melt flow stabilization to polypropylene.

EXAMPLE 21

Long Term Heat Aging Stabilization of Polypropylene

Extruded pellets prepared according to Example 20, after the first extrusion, are compression molded into 125 mil (3.2 mm) plaques at 450° F. (232° C.) and then oven aged at 150° C. in a forced draft oven. The time, in days, to reach a yellowness index (YI) color of 50 units is deemed to represent failure. The results are given in the table below.

| Additive* | Concentration (% by weight) | Days to Failure |
|---|---|---|
| AO A | 0.075 | 8 |
| AO A plus Example 14 Compound | 0.075 0.075 | 15 |

*AO A is neopentanetetrayl tetrakis(3,5-di-tert-butyl-4-hydroxyhydrocinnamate).

The combination of an instant compound plus a phenolic antioxidant nearly doubles the long term heat aging stability of the stabilized polypropylene over the use of a phenolic antioxidant alone.

EXAMPLE 22

Process Stabilization of Polypropylene at 525° F. (274° C.)

Following the procedure of Example 20, polypropylene containing a phenolic antioxidant in combination with an instant compound is extruded and the melt flow rate (in grams/10 minutes) determined by ASTM method D1238 on the pellets obtained from the extruder after each of the first and third extrusions. The results are given in the table below.

| Additive* | Concent. (% by wt) | Melt Flow Values after Extrusion 1 | 3 |
|---|---|---|---|
| AO A | 0.075 | 9.1 | 28.8 |
| AO A plus Example 8 Compound | 0.075 0.075 | 5.4 | 18.3 |
| AO A plus Example 10 Compound | 0.075 0.075 | 4.2 | 16.0 |
| AO A plus Example 12 Compound | 0.075 0.075 | 6.9 | 22.1 |
| AO A plus Example 14 | 0.075 0.075 | 4.9 | 17.5 |

*AO A is neopentanetetrayl tetrakis(3,5-di-tert-butyl-4-hydroxyhydrocinnamate).

The combination of a phenolic antioxidant plus an instant compound provides excellent melt flow stabilization; better stabilization than obtained by the use of a phenolic antioxidant alone.

What is claimed is:

1. A stabilized composition which comprises
(A) an organic material subject ot oxidative, thermal or actinic degradation, and
(B) an effective stabilizing amount of a bisphosphite of formula I, or III

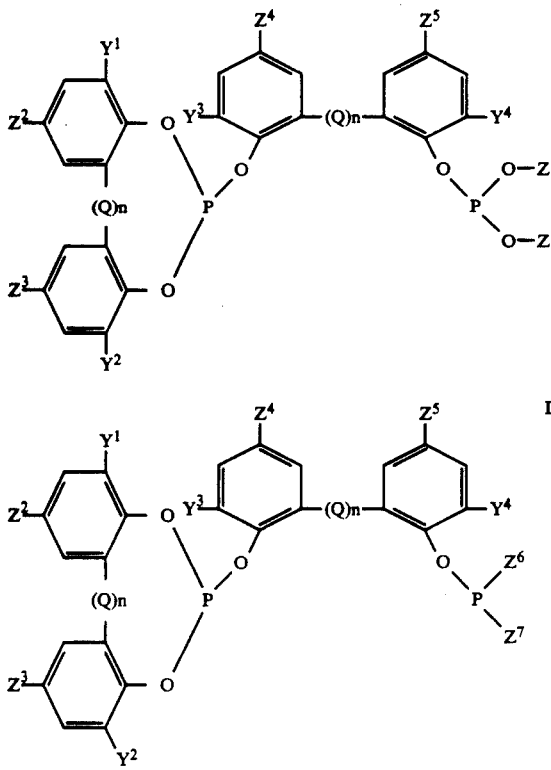

wherein n has a value of 0 or 1;

when n is 0, Q is a direct bond, when n is 1, Q is —CR$^1$R$^2$ wherein each R$^1$ and R$^2$ independently represents hydrogen, straight chain alkyl of 1 to 18 carbon atoms, branched chain alkyl of 1 to 12 carbon atoms, phenyl, tolyl or anisyl;

each Y$^1$, Y$^2$, Y$^3$, Y$^4$, Z$^2$, Z$^3$, Z$^4$ and Z$^5$ independently represents hydrogen, a straight or branched chain alkyl of 1 to 18 carbon atoms, bicycloalkyl of 7 to 10 carbon atoms, phenyl, benzyl, 1-phenylethyl, cyclohexyl, 1-methylcyclohexyl, cyano, halogen, nitro, trifluoromethyl, hydroxy, amino, alkanoyl of 2 to 18 carbon atoms, alkoxy of 1 to 18 carbon atoms or E$^1$E$^2$E$^3$Si where E$^1$, E$^2$ and E$^3$ are independently hydrogen, alkyl of 1 to 4 carbon atoms or phenyl;

each Z independently represents alkyl of 1 to 18 carbon atoms, phenyl or said phenyl mono- or di-substituted by alkyl of 1 to 8 carbon atoms or 1-phenylethyl; or by cyano, halogen, nitro, trifluoromethyl, hydroxy, amino, alkanoyl of 2 to 18 carbon atoms, alkoxy of 1 to 18 carbon atoms or E$^1$E$^2$E$^3$Si where E$^1$, E$^2$ and E$^3$ are independently hydrogen, alkyl of 1 to 4 carbon atoms or phenyl; and Z$^6$ and Z$^7$ are independently hydrogen, a straight or branched chain alkyl of 1 to 18 carbon atoms, phenyl, said phenyl substituted by alkyl of 1 to 8 carbon atoms; or are independently benzyl, 1-phenylethyl, cyclohexyl, 1-methylcyclohexyl, cyano, halogen, —NR$^3$R$^4$, and —SR$^5$ where R$^3$, R$^4$ and R$^5$ are independently hydrogen, a straight or branched chain alkyl of 1 to 18 carbon atoms, phenyl, benzyl, cyclohexyl or 1-methylcyclohexyl.

2. A composition according to claim 1 wherein the organic material is a synthetic polymer.

3. A composition according to claim 2 wherein the polymer is a polyolefin.

4. A composition according to claim 3 wherein the polyolefin is polypropylene.

5. A composition according to claim 1 wherein component (A) is polypropylene, and component (B) is a compound of formula I where Z is phenyl, Q is a direct bond or ethylidene, and Y$^1$, Y$^2$, Y$^3$, Y$^4$, Z$^2$, Z$^3$, Z$^4$ and Z$^5$ are each tert-butyl.

6. A composition according to claim 1 wherein the compound of component (B) is:

(a) 1-O-(2,4,8,10-Tetra-tert-butyl-dibenzo[d,f][1,3,2-]dioxaphosphepin-6-yl)-1'-O'-(diphenoxyphosphino)-2,2'-ethylidenebis(4,6-di-tert-butylphenol);

(b) 2-O-(2,4,8,10-tetra-tert-butyl-dibenzo[d,f][1,3,2-]dioxaphosphepin-6-yl)-2'-O'-(diphenoxy-phosphino)-3,3',5,5'-tetra-tert-butyl-2,2'-dihydroxy-1,1'-biphenyl;

(c) 1-O-(2,4,8,10-Tetra-tert-butyl-12-methyl-12H-dibenzo[d,g][1,3,2]dioxaphosphocin-6-yl)-1'-O'-(diphenoxyphosphino)-2,2'-ethylidenebis(4,6-di-tert-butylphenol);

(d) 1-O-(2,4,8,10-Tetra-tert-butyl-dibenzo[d,f][1,3,2-]dioxaphosphepin-6-yl)-1'-O'-(diphenoxyphosphino)-2,2'-methylenebis(4,6-di-tert-butylphenol);

(e) 1-O-(2,4,8,10-tetra-tert-butyl-12H-dibenzo[d,g][1,3,2]dioxaphosphocin-6-yl)-1'-O'-(diphenoxyphino)-2,2'-methylenebis(4,6-di-tert-butylphenol);

(f) 1-O-(2,4,8,10-Tetra-tert-butyl-dibenzo[d,f][1,3,2-]dioxaphosphepin-6-yl)-1'-O'-(diphenylphosphino)-2,2'-ethylidenebis(4,6-di-tert-butylphenol); or (g) 1-O-(2,4,8,10-tetra-tert-butyl-12-methyl-12H-dibenzo[d,g][1,3,2]dioxaphosphocin-6-yl)-1'-O'-(diphenylphosphino)-2,2'-ethylidenebis(4,6-di-tert-butylphenol).

7. A composition according to claim 6 which additionally contains an effective stabilizing amount of a phenolic antioxidant.

8. A composition according to claim 7 wherein the phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydrocinnammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

9. A composition according to claim 8 wherein the phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)-benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

10. A composition according to claim 6 which additionally contains an effective stabilizing amount of a hindered amine compound.

11. A composition according to claim 10 wherein the hindered amine compound is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethyl-piperidin-4-yl/β,β,β',β'-tetramethyl-3,9-(2,4,8,10-tetraoxaspiro[5.5]-undecane) diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one) and bis(1-octyloxy-2,2,6,6-tetramethylpiperidin-4-yl) sebacate.

12. A composition according to claim 11 wherein the hindered amine is bis(2,2,6,6-tetramethylpiperidin-4-yl) sebacate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl) sebacate.

* * * * *